United States Patent
Power et al.

(10) Patent No.: US 10,092,712 B2
(45) Date of Patent: Oct. 9, 2018

(54) AEROSOL DELIVERY SYSTEM

(71) Applicant: Stamford Devices Limited, Galway (IE)

(72) Inventors: Patrick Joseph Power, County Galway (IE); Jimmy Eaton-Evans, Galway (IE)

(73) Assignee: Stamford Devices Limited, Galway (IE)

( * ) Notice: Subject to any disclaimer, the term of this patent is extended or adjusted under 35 U.S.C. 154(b) by 714 days.

(21) Appl. No.: 14/530,173

(22) Filed: Oct. 31, 2014

(65) Prior Publication Data

US 2015/0122248 A1    May 7, 2015

(30) Foreign Application Priority Data

Nov. 4, 2013 (EP) .................................. 13191432

(51) Int. Cl.
*A61M 11/02* (2006.01)
*A61M 16/20* (2006.01)
(Continued)

(52) U.S. Cl.
CPC ........ *A61M 11/02* (2013.01); *A61M 15/0021* (2014.02); *A61M 15/0085* (2013.01);
(Continued)

(58) Field of Classification Search
CPC .............. A61M 11/02; A61M 15/0021; A61M 15/0085; A61M 16/208; A61M 16/06;
(Continued)

(56) References Cited

U.S. PATENT DOCUMENTS

| 3,518,989 A | | 7/1970 | Seeler | |
| 3,769,973 A | * | 11/1973 | Esbenshade, Jr. .... | A61M 16/08 128/200.14 |

(Continued)

FOREIGN PATENT DOCUMENTS

WO    WO 2012/046220 A    4/2012

*Primary Examiner* — Gregory Anderson
*Assistant Examiner* — Jonathan Paciorek
(74) *Attorney, Agent, or Firm* — Bookoff McAndrews, PLLC

(57) ABSTRACT

A system for delivery of aerosol therapy to spontaneously breathing patients comprises a housing which defines a chamber. The housing has a base, a top and a main body extending between the base and the top. An ambient air inlet is located adjacent to the base and is normally closed by an inlet valve. The housing also has a patient port for receiving a mouthpiece or a face mask. The mouthpiece has an exhaust outlet closed by an exhaust valve. Similarly, the face mask has an exhaust outlet closed by an exhaust valve. Exhaled air is exhausted through the valves and to prevent recirculation through the chamber which would adversely affect dose efficiencies. The housing also has an aerosol port for receiving a vibrating mesh aerosol generating device. The aerosol port is located in a side of the main body of the housing for delivery of aerosol into the chamber between the inlet valve and the patient port. A boss extends upwardly from the base and is spaced-apart inwardly of the main body of the housing to define a reception space or well.

17 Claims, 8 Drawing Sheets

(51) Int. Cl.
*A61M 15/00* (2006.01)
*A61M 16/06* (2006.01)
*A61M 11/00* (2006.01)

(52) U.S. Cl.
CPC .......... *A61M 16/06* (2013.01); *A61M 16/208* (2013.01); *A61M 11/003* (2014.02); *A61M 2202/0208* (2013.01); *A61M 2202/04* (2013.01)

(58) Field of Classification Search
CPC ........ A61M 11/003; A61M 2202/0208; A61M 2202/04
See application file for complete search history.

(56) References Cited

U.S. PATENT DOCUMENTS

| | | | |
|---|---|---|---|
| 5,540,221 A | 7/1996 | Kaigler et al. | |
| 5,617,844 A | 4/1997 | King | |
| 5,738,087 A * | 4/1998 | King | A61M 15/0086 128/200.23 |
| 6,138,668 A | 10/2000 | Patton et al. | |
| 6,235,177 B1 | 5/2001 | Borland et al. | |
| 7,066,398 B2 | 6/2006 | Borland et al. | |
| 7,204,245 B2 * | 4/2007 | Johnson | A61M 15/0086 128/200.14 |
| 8,151,794 B2 * | 4/2012 | Meyer | A61M 15/0086 128/200.22 |
| 2001/0013341 A1 * | 8/2001 | Gallem | A61M 15/0086 128/200.14 |
| 2005/0011514 A1 * | 1/2005 | Power | A61M 15/0085 128/200.14 |
| 2007/0023547 A1 | 2/2007 | Borland et al. | |
| 2007/0267010 A1 | 11/2007 | Fink et al. | |
| 2011/0108025 A1 * | 5/2011 | Fink | A61M 11/005 128/200.16 |
| 2012/0145148 A1 | 6/2012 | Meyer et al. | |

* cited by examiner

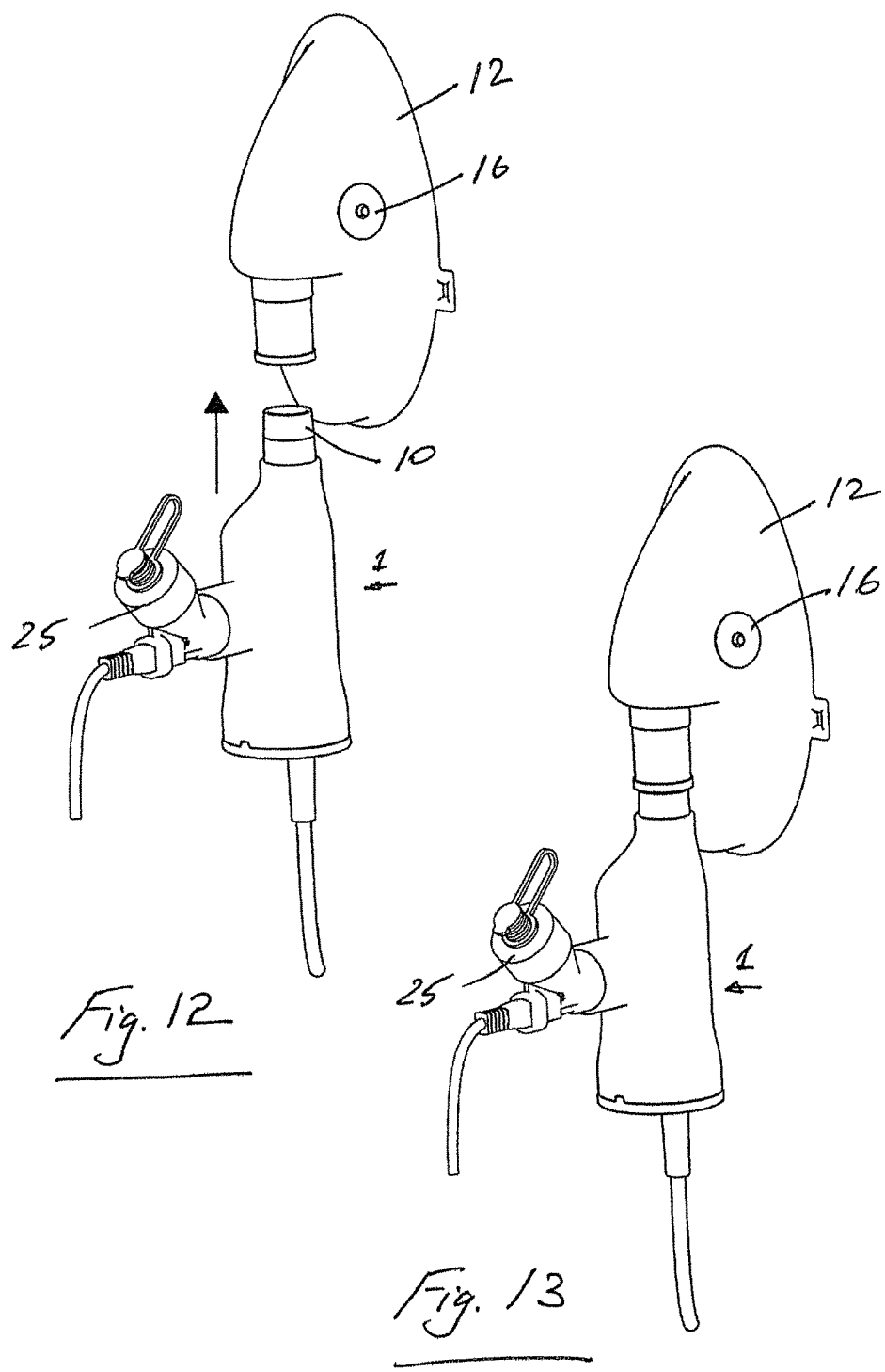

AEROSOL DELIVERY SYSTEM

INTRODUCTION

This invention relates to the delivery of aerosol to patients in response to spontaneous breathing.

US2011/0108025 describes an aerosol transfer device coupled to a nebuliser which generates an aerosol plume and to a patient interface. Upon inhalation by a patient ambient air is drawn into the device and flows counter-currently to the aerosol plume. However, the device is relatively large and cumbersome for use and complex to manufacture. It is also restricted to particular uses

STATEMENTS OF INVENTION

According to the invention there is provided an aerosol delivery device comprising a housing defining a chamber, the housing having:
   a base;
   a top;
   a main body extending between the base and the top;
   an air inlet closed by an inlet valve, the air inlet being located adjacent to the base of the housing;
   a patient port for receiving a mouthpiece or a face mask, the mouthpiece or face mask having an exhaust outlet closed by an exhaust valve; and
   an aerosol port for receiving a vibrating mesh aerosol generating device, the aerosol port being located in a side of the main body of the housing for delivery of aerosol into the chamber between the inlet valve and the patient port,
   the inlet valve being breath actuatable for movement between an inspiration configuration in which the inlet valve is open and an exhalation configuration in which the inlet valve is closed.

In one embodiment the housing comprises a boss extending from the base of the housing and being spaced-apart inwardly of the main body of the housing to define a reception space.

In one case the inlet valve is mounted to the boss for movement between the open and closed configurations. The boss may comprise a raised region against which a portion of the inlet valve is seated. The raised region may be defined by a rim which extends at least partially around the boss.

In one embodiment the housing comprises an oxygen supply port for connection to a supply of oxygen. The oxygen supply port may be normally closed by the inlet valve. In one case the oxygen supply port is located within the margins of the boss.

In one embodiment a longitudinal axis through a center of the aerosol inlet port is substantially at right angles with respect to a longitudinal axis through the main body of the housing.

In one case a longitudinal axis through a center of the patient port is offset from a longitudinal axis through a center of the inlet. The main body of the housing may comprise a tapered transition section to the patient port.

The invention also provides an aerosol delivery system comprising an aerosol deliver device of the invention and a mouth piece or a face mask for connection to the patient port.

In a preferred embodiment the mouthpiece or face mask comprises an exhaust outlet closed by an exhaust valve, the inlet and exhaust valves being breath actuated from an inspiration configuration in which the inlet valve is open and the exhaust valve is closed to an exhalation configuration in which the inlet valve is closed and the exhaust valve is open.

In one case a longitudinal axis through a center of the patient port of the mouth piece subtends on angle of from 0° to 90° with a longitudinal axis of the main body of the housing. The angle may be approximately 60°.

In a further aspect the invention provides an aerosol delivery system further comprising a vibrating mesh aerosol generator for connection to the aerosol port for delivery of aerosol into inspiration gas flowing through the chamber when then inlet valve is open.

BRIEF DESCRIPTION OF THE DRAWINGS

The invention will be more clearly understood from the following description thereof, given by way of example in which:

FIGS. 11 to 13 are isometric views of the device and an associated face mask.

DETAILED DESCRIPTION

Figure 1:
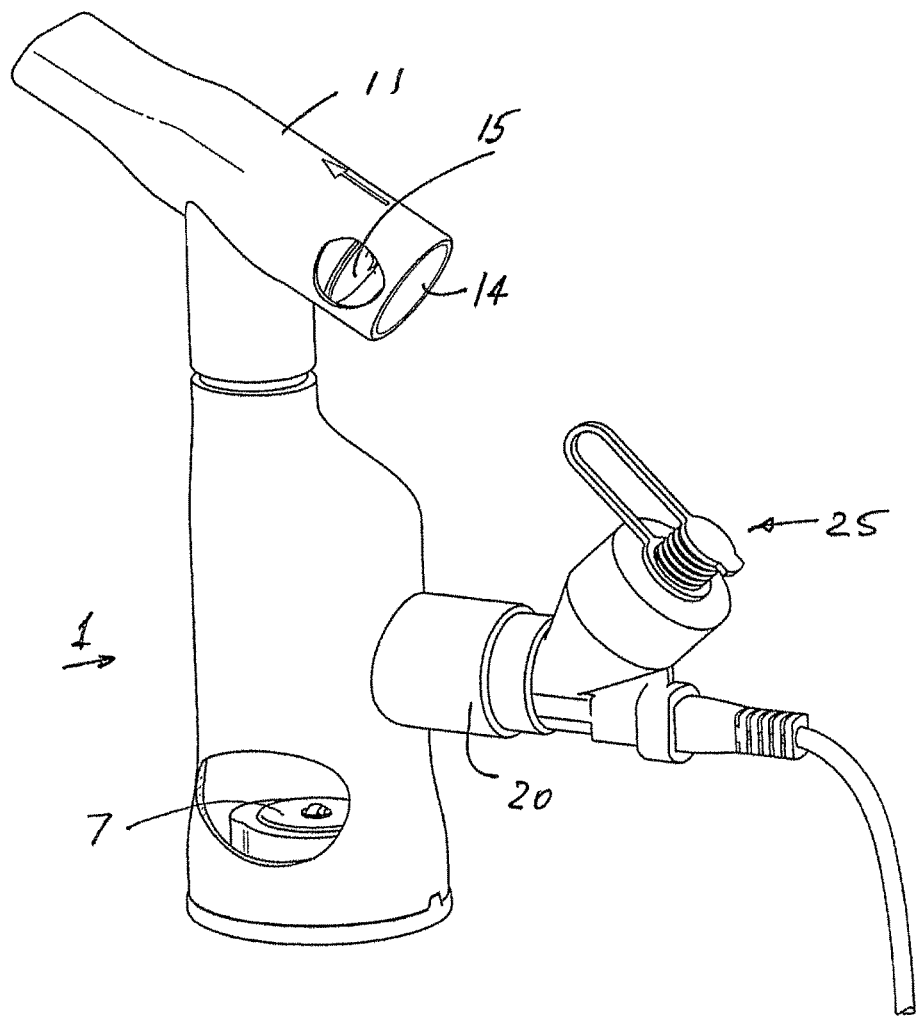
FIG. 1 is an isometric, partially cut-away view of an aerosol delivery system according to the invention.
Figure 2:
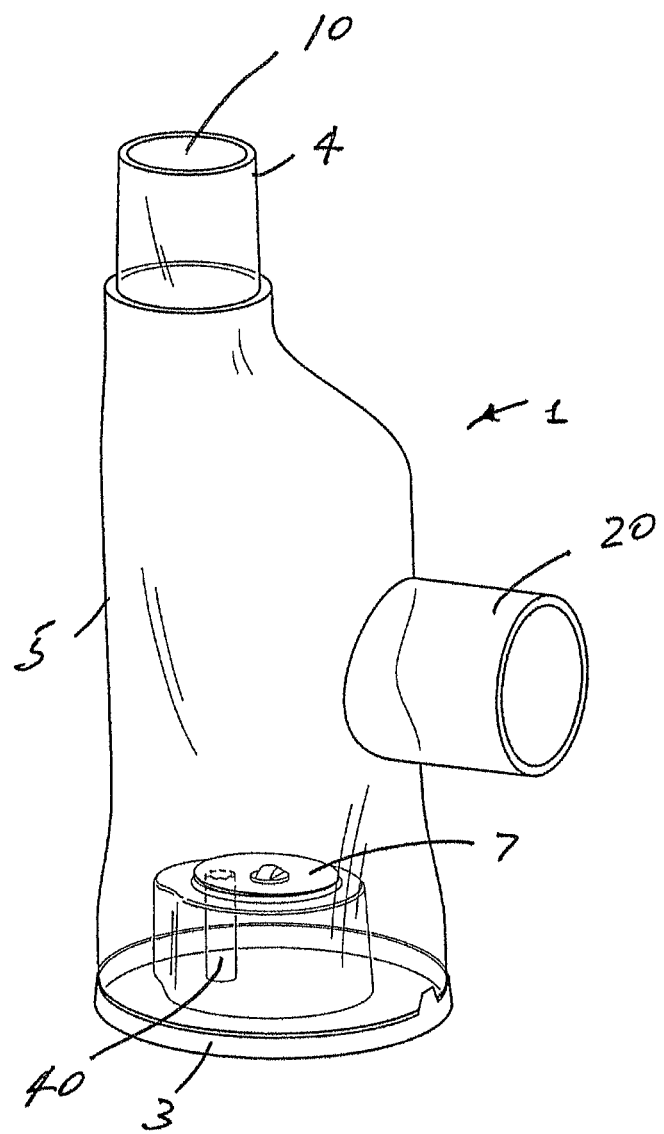
FIG. 2 is an isometric view of an aerosol delivery device of the invention forming part of the system of FIG. 1.
Figure 3:
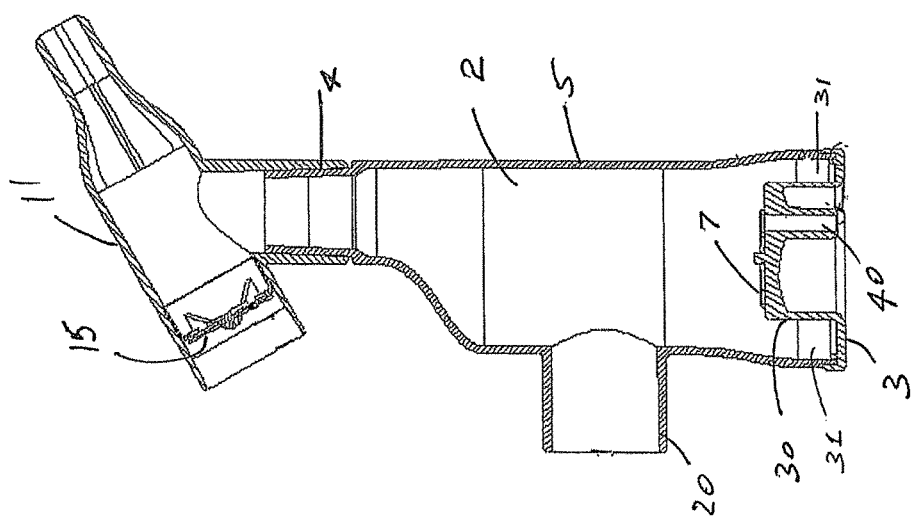
FIGS. 3 and 4 are cross sectional views of the aerosol delivery system of FIG. 1.

The invention provides a system for delivery of aerosol therapy to spontaneously breathing patients.

Referring to the drawings there is illustrated an aerosol delivery device according to the invention which comprises a housing 1 which defines a chamber 2. The housing has a base 3, a top 4 and a main body 5 extending between the base 3 and the top 4. An ambient air inlet 6 is located adjacent to the base 3 and is normally closed by an inlet valve 7.

The housing also has a patient port 10 for receiving a mouthpiece 11 or a face mask 12. The mouthpiece 11 has an exhaust outlet 14 closed by an exhaust valve 15. Similarly, the face mask 12 has an exhaust outlet closed by an exhaust valve 16. Exhaled air is exhausted through the valves 15 and 16 to prevent recirculation through the chamber 2 which would adversely affect dose efficiencies.

The housing also has an aerosol port 20 for receiving a vibrating mesh aerosol generating device 25. The aerosol port 20 is located in a side of the main body of the housing 1 for delivery of aerosol into the chamber 2 between the inlet valve 7 and the patient port 10, generally perpendicular to the flow of air through the chamber 2.

The inlet valve 7 and the exhaust valves 15, 16 are one-way breath actuated and move from an inspiration configuration in which the inlet valve 7 is open and the exhaust valve 15,16 is closed to an exhalation configuration in which the inlet valve 7 is closed and the exhaust valve 15,16 is open.

The housing 1 comprises a boss 30 extending upwardly from the base 3. The boss is spaced-apart inwardly of the main body 5 of the housing 1 to define a reception space or well 31. This facilitates collection of any rain-out within the chamber 2. The inlet valve 7 is of a flexible polymeric material such as Elastosil R401-40 (Wacker, Munich, Germany) and has a receiver for mounting to a mounting element 33. The valve 7 is movable relative to the boss 30 between the open and closed configuration. The boss 30 also has a raised region which in this case is defined by a rim 35 which extends around the boss 30 to lift one section of the valve 7. This assists in preventing adhesion between the valve 7 and the boss 30 and facilitates opening of the valve even if the inhalation force applied is low.

The housing 2 also has an oxygen supply port 40 for connection to a supply of supplemental oxygen. In this case the oxygen supply port 40 is located in the base 3 of the device within the margins of the boss 30 and is normally closed by the inlet valve 7. Thus, the inlet valve occludes the oxygen port when no oxygen flow is connected, thus maximising device efficiency. When an oxygen supply is connected the valve 7 opens. This arrangement avoids the necessity for a separates cap or valve on the oxygen supply port and diffuses oxygen flow entering the chamber 2 which improves the efficiency of the device.

It will be noted that a longitudinal axis through a center of the aerosol delivery port 20 is substantially at right angles with respect to a longitudinal axis through the main body of the housing 1. This feature assists in reducing aerosol impaction and therefore maximises dose efficiency during changes in flow direction associated with inhalation and exhalation. It also facilitates nebuliser placement for cable management and device usability.

A longitudinal axis through a center of the patient port 10 is offset from a longitudinal axis through a center of the air inlet. This feature also assists in reducing aerosol impaction and therefore maximises dose efficiency. This optimum placement also minimises device size and therefore maximises usability.

The main body of the housing 1 comprises a tapered transition section 50 to the patient port 10. This provides minimum resistance to flow and minimises rain-out whilst maximising efficiency.

Figure 4:
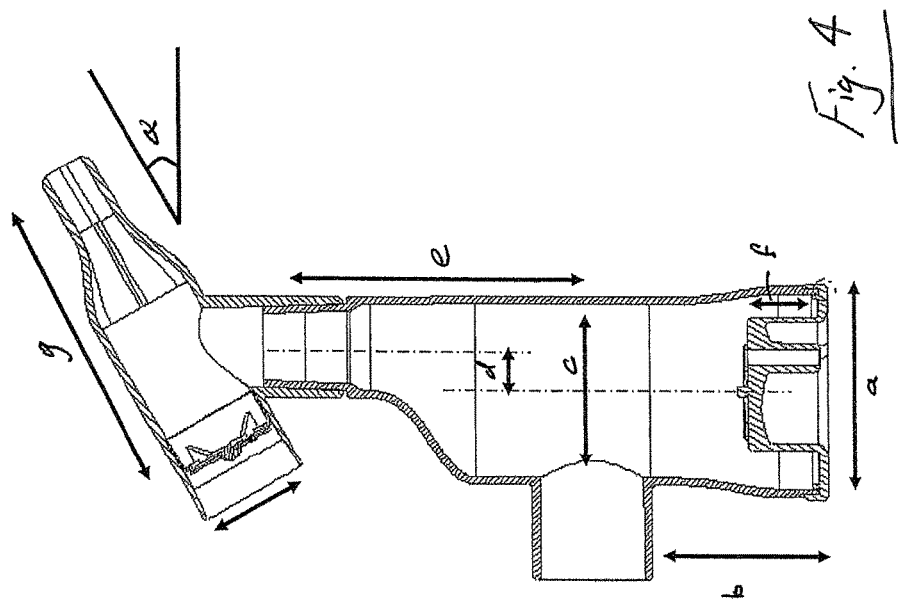
Figure 5:
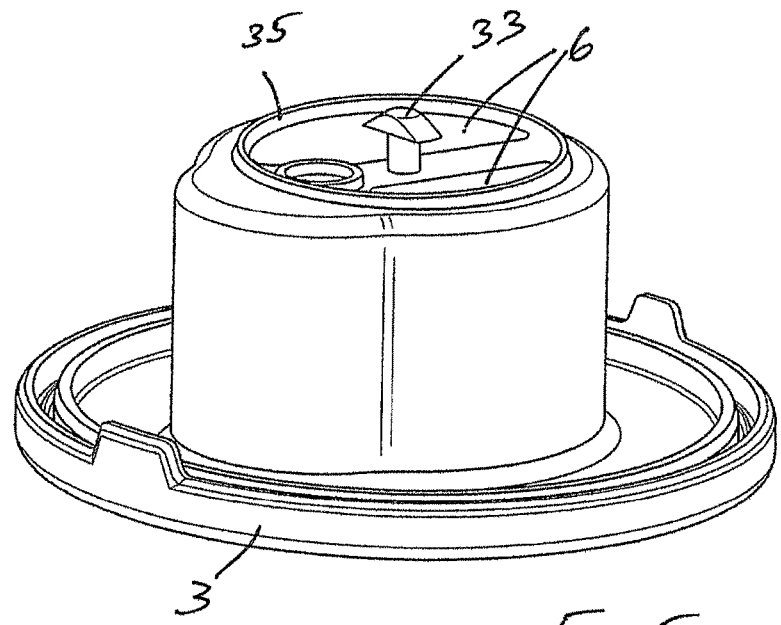
FIG. 5 is an isometric view of an air inlet end of the device with a valve removed.
Figure 8:
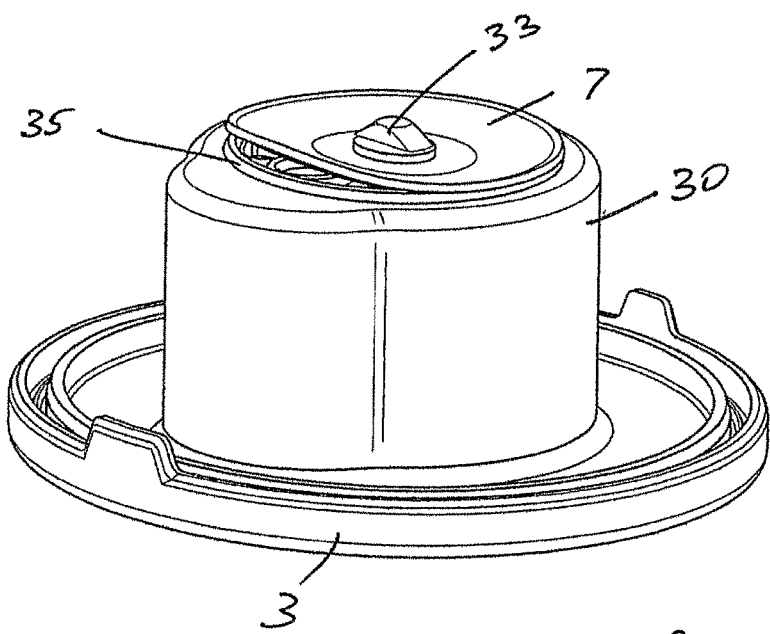
FIG. 8 is an isometric view of the air inlet end of the device with a valve in situ.
Figure 6:
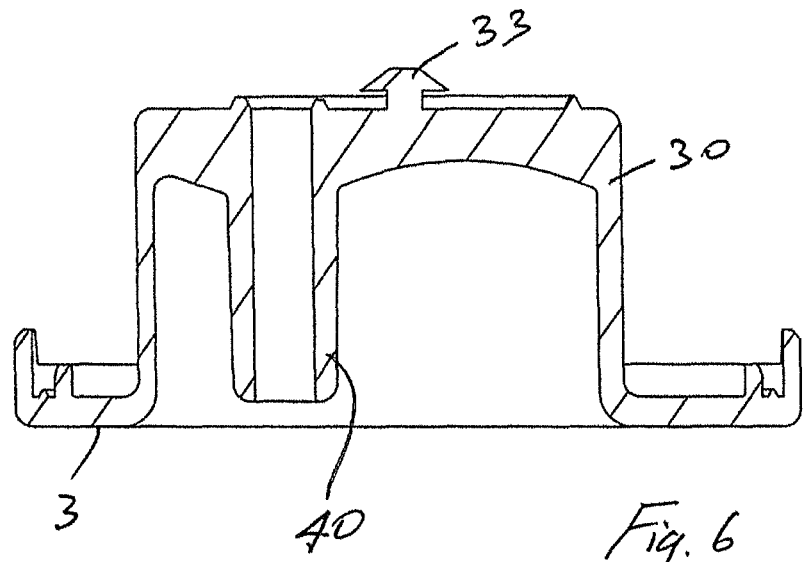
FIGS. 6 and 7 are cross sectional views of the air inlet end of FIG. 5.
Figure 7:
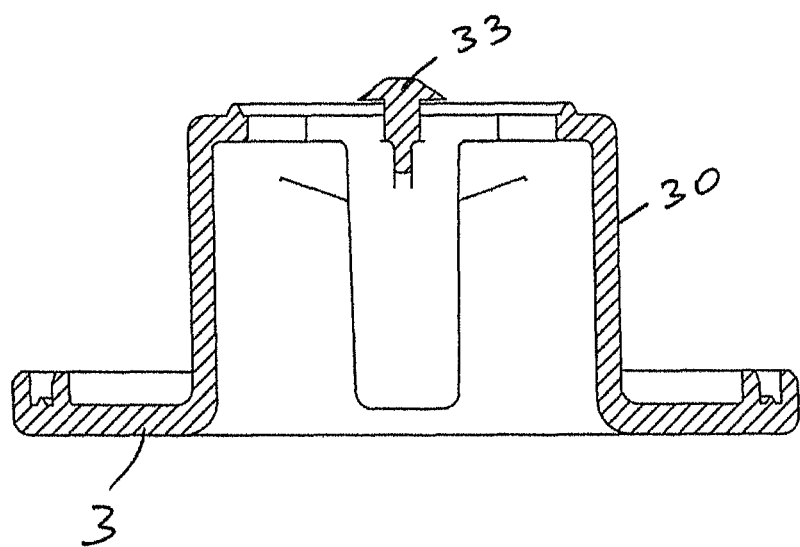
Figure 9:
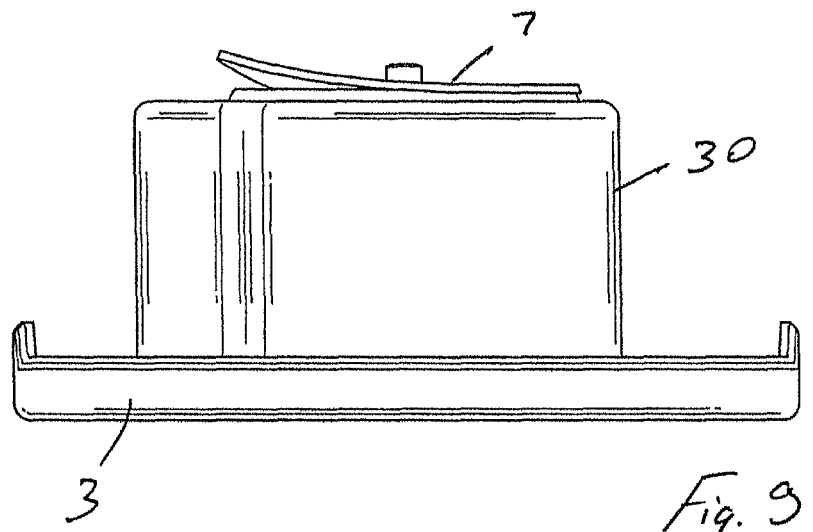
FIGS. 9 to 10 are elevational and cross sectional views of the air inlet end of FIG. 8.
Figure 10:
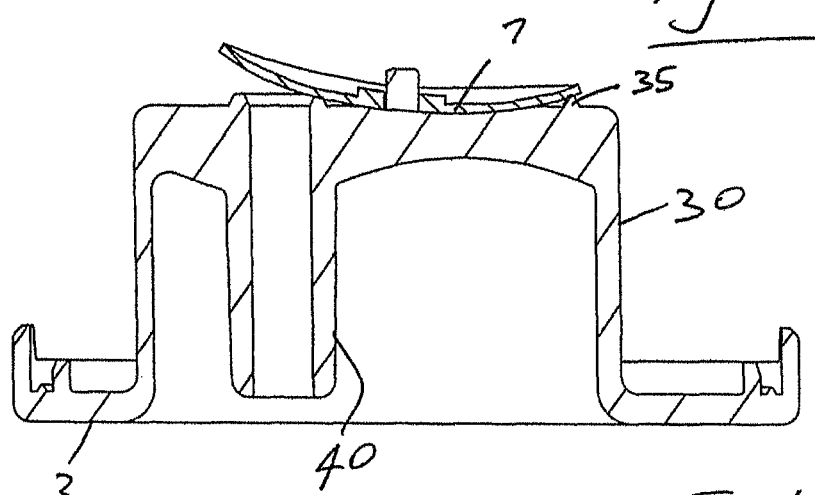
Figure 11:
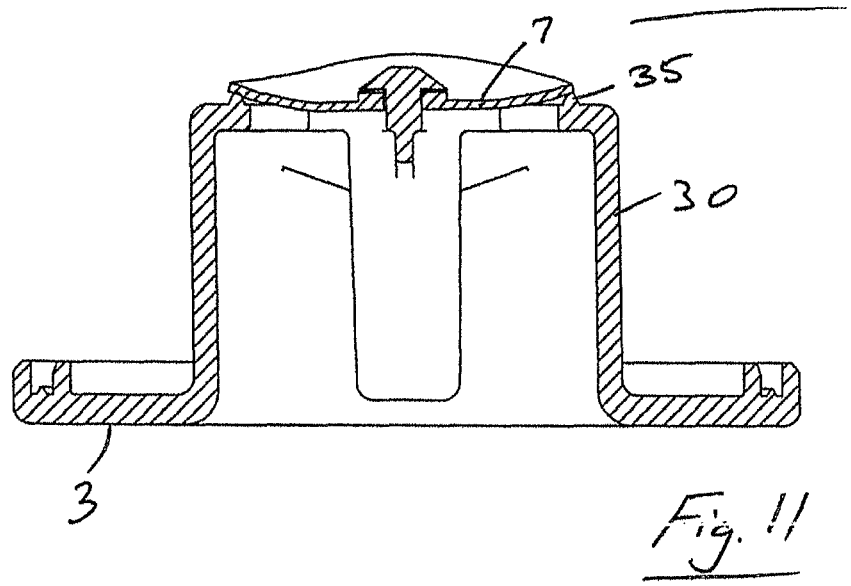

Referring in particular to FIG. 4, it will also be noted that a longitudinal axis through a center of the patient port of the mouth piece subtends an angle α of from about 0° to about 90°, in this case approximately 60° to the main body of the housing. This also maximises dose efficiency.

Referring in particular to FIG. 4 the dimensions a to h are important in optimising device efficiency. The approximate values for these dimensions are as follows.

a: range 40-60 optimum approximately 46 mm
b: range 22-66 optimum approximately 39 mm
c: range 25-45 optimum approximately 37 mm
d: range 0-10 optimum approximately 9 mm
e: range 50-90 optimum approximately 67 mm
f: range 17-25 optimum approximately 17 mm
g: range 70-90 optimum approximately 70 mm
h: range 20-30 optimum approximately 24 mm In the invention high efficiency is achieved by:
Chamber design (i.e. diameter, length, etc.)
Neb positioning (i.e. perpendicular to chamber main axis, distance between neb and opposing wall and distance between neb and inlet valve)
Valves configuration to control the flow of air through the device
Angle of mouthpiece to chamber
Alignment of chamber outlet with bottom wall
Use of inlet valve to diffuse flow oxygen into the device Rainout management is achieved by:
Inlet valve is located in a raised position ensure it does not contact rainout
Inlet valve seals on raised rim to reduce adhesion due to rainout
Inlet valve seal design to lift one section of valve to reduce the pressure differential required to open valve The system can be used with or without supplementary oxygen.

The aerosol generator 25 is a vibrating mesh type nebuliser as described in our WO2012/046220A, the entire contents of which are incorporated herein by reference.

Aerosol generators comprising a vibratable member and a plate body operably coupled to the vibratable member are known, the plate body has a top surface, a bottom surface, and a plurality of apertures extending from the top surface to the bottom surface. The apertures may be tapered such that when a liquid is supplied to one surface and the aperture plate is vibrated using the vibratable member, liquid droplets are ejected from the opposite surface. Details of such known systems are described for example in U.S. Pat. No. 6,235,177, US2007/0023547A, and U.S. Pat. No. 7,066,398, the entire contents of which are herein incorporated by reference.

The invention may be used to provide treatments for a variety of aliments using a variety of aerosolisable medicaments. The ailments may include pulmonary ailments such as ventilator-associated pneumonia, hospital-acquired pneumonia, community-acquired pneumonia, asthma, cystic fibrosis, mycobacterial infection, mucociliary clearance conditions, bronchitis, staph infection, fungal infections, viral infections, tuberculosis, protozoal infections, emphysema, hereditary emphysema, Chronic Obstructive Pulmonary Disease (COPD) and acute exacerbation of COPD, among others. The aerosolizable medicaments used to treat the ailments may include antitrypsins (such as alpha-1 antitrypsin), antibiotics, anti-infectives, antivirals, anti-oxidants, epithelium sodium channel blockers, bronchodilators, beta-antagonists (short and long acting) corticosteroids, leukotrienes, protease inhibitors, surfactants, and vaccines, among other medicaments. The ailments may further include non-pulmonary-related, such as systemic conditions, such as diabetes, cancer, immune diseases, cardiovascular conditions, metabolic diseases and the like.

The invention may be used in a method of treating a patient by administering to the patient any desirable nebulised dose of aerosol.

In some cases the method of treating a patient involves administering to the patient a discrete nebulised dose of aerosol comprising from 0.05 mL to about 50 mL of a medicament or greater than 50 mL when administering continuous aerosol therapy.

Also provided are methods of treatment by administering to a patient an aerosolised formulation comprising an anti-infective dissolved in an aqueous solution that is adjusted to a pH between about 3.0 and 10.5.

In some cases the medicament is administered continuously.

In other cases the medicament is administered intermittently.

The systems are configurable to administer aerosolised medicament, such as an anti-infective, to a spontaneous-breathing patient.

Substantially all of the device may be reused for multiple treatments with a single patient before disposing thereof.

The device may be used for only a single patient, then disposed.

A filter can be positioned at the exhaust outlet to capture exhausted drug.

The invention is not limited to the embodiments hereinbefore described, which may be varied in construction and detail.

The invention claimed is:

1. An aerosol delivery device comprising a housing defining a chamber, the housing having:

a base;

a top;

a main body extending between the base and the top;

an air inlet selectively closed by an inlet valve, the air inlet being located adjacent to the base of the housing;

an oxygen supply port selectively closed by the inlet valve and including a central longitudinal axis parallel to a central longitudinal axis of the air inlet;

a patient port for coupling to a patient interface, wherein a longitudinal axis of the patient port is parallel with the central longitudinal axis of the air inlet; and an aerosol port for receiving an aerosol generating device, the aerosol port being located in a side of the main body of the housing for delivery of aerosol into the chamber between the inlet valve and the patient port, the inlet valve being breath actuatable for movement between an inspiration configuration in which the inlet valve is open and an exhalation configuration in which the inlet valve is closed.

2. An aerosol delivery device as claimed in claim 1 wherein the housing comprises a boss extending from the base of the housing and spaced radially inwardly of the main body of the housing to define a reception space therebetween.

3. An aerosol delivery device as claimed in claim 2 wherein the inlet valve is mounted to the boss for movement between the inspiration configuration and the exhalation configuration.

4. An aerosol delivery device as claimed in claim 3 wherein the boss comprises a raised region against which a portion of the inlet valve is seated.

5. An aerosol delivery device as claimed in claim 4 wherein the raised region is defined by a rim which extends partially around the boss.

6. An aerosol delivery device as claimed in claim 1 wherein the oxygen supply port is normally closed by the inlet valve.

7. An aerosol delivery device as claimed in claim 1 wherein the oxygen supply port is located within the margins of the boss.

8. An aerosol delivery device as claimed in claim 1 wherein a longitudinal axis through a center of the aerosol port is orthogonal to a longitudinal axis through the main body of the housing.

9. An aerosol delivery device as claimed in claim 1 wherein the main body of the housing comprises a tapered transition section.

10. An aerosol delivery device comprising a housing defining a chamber, the housing having:

a base;

a top located opposite the base;

a main body extending between the base and the top;

an air inlet located in the base and selectively closed by an inlet valve;

an oxygen supply port having a central longitudinal axis parallel with a central longitudinal axis of the air inlet;

a patient port for coupling to a patient interface; and an aerosol port for delivery of aerosol into the chamber between the inlet valve and the patient port, the inlet valve being breath actuatable for movement between an inspiration configuration in which the inlet valve is open and an exhalation configuration in which the inlet valve is closed.

11. An aerosol delivery device as claimed in claim 10 wherein the oxygen supply port is located in the base.

12. An aerosol delivery device as claimed in claim 11 wherein both the oxygen supply port and the air inlet are coupled to the inlet valve.

13. An aerosol delivery device as claimed in claim 11, wherein a longitudinal axis through a center of the aerosol port is orthogonal to a longitudinal axis through the main body of the housing.

14. A system for aerosol delivery including:

a housing defining a chamber, the housing including:

a base;

a top located opposite the base;

a main body extending between the base and the top;

an air inlet located in the base and selectively closed by an inlet valve;

a patient port located at the top; and an aerosol port for delivery of aerosol into the chamber between the inlet valve and the patient port, the inlet valve located in the base and being breath actuatable for movement between an inspiration configuration in which the inlet valve is open and an exhalation configuration in which the inlet valve is closed; and a patient interface coupled to the patient port and including an exhaust outlet, wherein the patient interface includes a central longitudinal axis extending at an angle offset with respect to both a central longitudinal axis of the aerosol port and a central longitudinal axis of the main body.

15. The system as claimed in claim 14 wherein the patient interface includes at least one of a mouth piece or a face mask.

16. The system as claimed in claim 14 wherein the exhaust outlet is selectively closed by a breath-actuatable exhaust valve.

17. The system as claimed in claim 14, wherein a longitudinal axis through a center of the aerosol port is orthogonal to a longitudinal axis through the main body of the housing.

* * * * *